United States Patent [19]

Rudolph et al.

[11] Patent Number: 5,077,392
[45] Date of Patent: Dec. 31, 1991

[54] PROCESS FOR ACTIVATION OF RECOMBINANT PROTEIN PRODUCED BY PROKARYOTES

[75] Inventors: Rainer Rudolph, Weilheim; Johannes Buchner, Regensburg; Helmut Lenz, Tutzing, all of Fed. Rep. of Germany

[73] Assignee: Boehringer Mannheim GmbH, Mannheim, Fed. Rep. of Germany

[21] Appl. No.: 422,948

[22] Filed: Oct. 17, 1989

[30] Foreign Application Priority Data

Oct. 17, 1988 [DE] Fed. Rep. of Germany ....... 3835350

[51] Int. Cl.$^5$ .................... C07K 3/00; C07K 15/00; C07K 15/28; C12N 9/50
[52] U.S. Cl. .................................. 530/402; 530/408; 530/409; 530/387; 435/219; 424/94.64
[58] Field of Search ............... 530/387, 402, 408, 409; 424/85.8, 94.64, 94.63; 435/215, 219

[56] References Cited

U.S. PATENT DOCUMENTS

| | | | |
|---|---|---|---|
| 4,620,948 | 11/1986 | Builder et al. | 530/419 |
| 4,634,586 | 1/1987 | Goodwin et al. | 424/1.1 |
| 4,766,205 | 8/1988 | Ghosh-Dastidar et al. | 530/402 |
| 4,816,567 | 3/1989 | Cabilly et al. | 530/387 |
| 4,933,434 | 6/1990 | Rudolph et al. | 530/405 |

FOREIGN PATENT DOCUMENTS

| | | |
|---|---|---|
| 0114506 | 8/1984 | European Pat. Off. . |
| 0192629 | 8/1986 | European Pat. Off. . |
| 0211592 | 2/1987 | European Pat. Off. . |
| 0219874 | 4/1987 | European Pat. Off. . |
| 0236209 | 9/1987 | European Pat. Off. . |
| 0241022 | 10/1987 | European Pat. Off. . |
| 2176702 | 11/1987 | United Kingdom . |
| WO8702985 | 5/1987 | World Int. Prop. O. . |

OTHER PUBLICATIONS

Freedman et al., J. Biol. Chem. 241(22): 5225–5232, (1966), Chem. Abst. 113(3): 21920S, (1990).

*Primary Examiner*—Garnette D. Draper
*Assistant Examiner*—R. Keith Baker
*Attorney, Agent, or Firm*—Felfe & Lynch

[57] ABSTRACT

The present invention provides a process for the activation of gene-technologically produced, biologically active proteins expressed in prokaryotes after cell digestion by solubilization under denaturing conditions and reducing conditions and subsequent reactivation under oxidizing and renaturing conditions, wherein working is carried out at a protein concentration of 1 to 1000 μg./ml. and, between the solubilization and the reactivation, a dialysis is carried out against a buffer with a pH value of from 1 to 4 containing 4 to 8 mole/liter guanidine hydrochloride or 6 to 10 mole/liter urea.

28 Claims, 3 Drawing Sheets

FIG. 1A.

```
   1  TTCATGGATATTGTGCTAACTCAGTCTCCAGCCACCCTGTCTGTGACTCCAAGAGATAGC
  61  GTCAGTCTTTCCTGCAGGGCCAGCCAAAGTATTAGCAACAACCTACACTGGTATCAACAA
 121  AAATCACATGAGTCTCCAAGGCTTCTCATCAAATATGCTTCCCAGTCCATCTCTGGGATC
 181  CCCTCTAGGTTCAGTGGCAGTGGATCAGGGACAGATTTCACTCTCAGTATCAACAGTGTG
 241  GAGACTGAAGATTTTGGAATGTATTTCTGTCAACAGAGTAACAGCTGGCCTCTCACGTTC
 301  GGTGCTGGGACCAAGCTGGAGCTGAAACGGGCTGATGCTGCACCAACTGTATCCATCTTC
 361  CCACCATCCAGTGAGCAGTTAACATCTGGAGGTGCCTCAGTCGTGTGCTTCTTGAACAAC
 421  TTCTACCCCAAAGACATCAATGTCAAGTGGAAGATTGATGGCAGTGAACGACAAAATGGC
 481  GTCCTGAACAGTTGGACTGATCAGGACAGCAAAGACAGCACCTACAGCATGAGCAGCACC
 541  CTCACGTTGACCAAGGACGAGTATGAACGACATAACAGCTATACCTGTGAGGCCACTCAC
 601  AAGACATCAACTTCACCCATTGTCAAGAGCTTCAACAGGAATGAGTGTTAGAGACAAAGG
 661  TCCTGAGACGCCACCACCAAAGCTTCTGTTTTGGCGGATGAGAGAAGATTTTCAGCCTGA
 721  TACAGATTAAATCAGAACGCAGAAGCGGTCTGATAAAACAGAATTTGCCTGGCGGCAGTA
 781  GCGCGGTGGTCCCACCTGACCCCATGCCGAACTCAGAAGTGAAACGCCGTAGCGCCGATG
 841  GTAGTGTGGGGTCTCCCCATGCGAGAGTAGGGAACTGCCAGGCATCAAATAAAACGAAAG
 901  GCTCAGTCGAAAGACTGGGCCTTTCGTTTTATCTGTTGTTTGTCGGTGAACGCTCTCCTG
 961  AGTAGGACAAATCCGCCGGGAGCGGATTTGAACGTTGCGAAGCAACGGCCCGGAGGGTGG
1021  CGGGCAGGACGCCCGCCATAAACTGCCAGGCATCAAATTAAGCAGAAGGCCATCCTGACG
1081  GATGGCCTTTTTGCGTTTCTACAAACTCTTTTGTTTATTTTTCTAAATACATTCAAATAT
1141  GTATCCGCTCATGAGACAATAACCCTGATAAATGCTTCAATAATATTGAAAAAGGAAGAG
1201  TATGAGTATTCAACATTTCCGTGTCGCCCTTATTCCCTTTTTTGCGGCATTTTGCCTTCC
1261  TGTTTTTGCTCACCCAGAAACGCTGGTGAAAGTAAAAGATGCTGAAGATCAGTTGGGTGC
1321  ACGAGTGGGTTACATCGAACTGGATCTCAACAGCGGTAAGATCCTTGAGAGTTTTCGCCC
1381  CGAAGAACGTTTTCCAATGATGAGCACTTTTAAAGTTCTGCTATGTGGCGCGGTATTATC
1441  CCGTGTTGACGCCGGGCAAGAGCAACTCGGTCGCCGCATACACTATTCTCAGAATGACTT
1501  GGTTGAGTACTCACCAGTCACAGAAAAGCATCTTACGGATGGCATGACAGTAAGAGAATT
1561  ATGCAGTGCTGCCATAACCATGAGTGATAACACTGCGGCCAACTTACTTCTGACAACGAT
1621  CGGAGGACCGAAGGAGCTAACCGCTTTTTTGCACAACATGGGGGATCATGTAACTCGCCT
1681  TGATCGTTGGGAACCGGAGCTGAATGAAGCCATACCAAACGACGAGCGTGACACCACGAT
1741  GCCTGTAGCAATGGCAACAACGTTGCGCAAACTATTAACTGGCGAACTACTTACTCTAGC
1801  TTCCCGGCAACAATTAATAGACTGGATGGAGGCGGATAAAGTTGCAGGACCACTTCTGCG
1861  CTCGGCCCTTCCGGCTGGCTGGTTTATTGCTGATAAATCTGGAGCCGGTGAGCGTGGGTC
1921  TCGCGGTATCATTGCAGCACTGGGGCCAGATGGTAAGCCCTCCCGTATCGTAGTTATCTA
1981  CACGACGGGGAGTCAGGCAACTATGGATGAACGAAATAGACAGATCGCTGAGATAGGTGC
2041  CTCACTGATTAAGCATTGGTAACTGTCAGACCAAGTTTACTCATATATACTTTAGATTGA
2101  TTTAAAACTTCATTTTTAATTTAAAAGGATCTAGGTGAAGATCCTTTTTGATAATCTCAT
2161  GACCAAAATCCCTTAACGTGAGTTTTCGTTCCACTGAGCGTCAGACCCCGTAGAAAAGAT
2221  CAAAGGATCTTCTTGAGATCCTTTTTTTCTGCGCGTAATCTGCTGCTTGCAAACAAAAAA
2281  ACCACCGCTACCAGCGGTGGTTTGTTTGCCGGATCAAGAGCTACCAACTCTTTTTCCGAA
2341  GGTAACTGGCTTCAGCAGAGCGCAGATACCAAATACTGTCCTTCTAGTGTAGCCGTAGTT
2401  AGGCCACCACTTCAAGAACTCTGTAGCACCGCCTACATACCTCGCTCTGCTAATCCTGTT
2461  ACCAGTGGCTGCTGCCAGTGGCGATAAGTCGTGTCTTACCGGGTTGGACTCAAGACGATA
2521  GTTACCGGATAAGGCGCAGCGGTCGGGCTGAACGGGGGGTTCGTGCACACAGCCCAGCTT
2581  GGAGCGAACGACCTACACCGAACTGAGATACCTACAGCGTGAGCTATGAGAAAGCGCCAC
2641  GCTTCCCGAAGGGAGAAAGGCGGACAGGTATCCGGTAAGCGGCAGGGTCGGAACAGGAGA
2701  GCGCACGAGGGAGCTTCCAGGGGGAAACGCCTGGTATCTTTATAGTCCTGTCGGGTTTCG
2761  CCACCTCTGACTTGAGCGTCGATTTTTGTGATGCTCGTCAGGGGGCGGAGCCTATGGAA
2821  AAACGCCAGCAACGCGGCCTTTTTACGGTTCCTGGCCTTTTGCTGGCCTTTTGCTCACAT
2881  GTTCTTTCCTGCGTTATCCCCTGATTCTGTGGATAACCGTATTACCGCCTTTGAGTGAGC
2941  TGATACCGCTCGCCGCAGCCGAACGACCGAGCGCAGCGAGTCAGTGAGCGAGGAAGCGGA
3001  AGAGCGCCTGATGCGGTATTTTCTCCTTACGCATCTGTGCGGTATTTCACACCGCATATG
3061  GTGCACTCTCAGTACAATCTGCTCTGATGCCGCATAGTTAAGCCAGTATACACTCCGCTA
3121  TCGCTACGTGACTGGGTCATGGCTGCGCCCCGACACCCGCCAACACCCGCTGACGCGCCC
3181  TGACGGGCTTGTCTGCTCCCGGCATCCGCTTACAGACAAGCTGTGACCGTCTCCGGGAGC
3241  TGCATGTGTCAGAGGTTTTCACCGTCATCACCGAAACGCGCGAGGCAGCTGCGGTAAAGC
3301  TCATCAGCGTGGTCGTGAAGCGATTCACAGATGTCTGCCTGTTCATCCGCGTCCAGCTCG
```

FIG. 1B.

```
3361  TTGAGTTTCTCCAGAAGCGTTAATGTCTGGCTTCTGATAAAGCGGGCCATGTTAAGGGCG
3421  GTTTTTTCCTGTTTGGTCACTTGATGCCTCCGTGTAAGGGGGAATTTCTGTTCATGGGGG
3481  TAATGATACCGATGAAACGAGAGAGGATGCTCACGATACGGGTTACTGATGATGAACATG
3541  CCCGGTTACTGGAACGTTGTGAGGGTAAACAACTGGCGGTATGGATGCGGCGGGACCAGA
3601  GAAAAATCACTCAGGGTCAATGCCAGCGCTTCGTTAATACAGATGTAGGTGTTCCACAGG
3661  GTAGCCAGCAGCATCCTGCGATGCAGATCCGGAACATAATGGTGCAGGGCGCTGACTTCC
3721  GCGTTTCCAGACTTTACGAAACACGGAAACCGAAGACCATTCATGTTGTTGCTCAGGTCG
3781  CAGACGTTTTGCAGCAGCAGTCGCTTCACGTTCGCTCGCGTATCGGTGATTCATTCTGCT
3841  AACCAGTAAGGCAACCCCGCCAGCCTAGCCGGGTCCTCAACGACAGGAGCACGATCATGC
3901  GCACCCGTGGCCAGGACCCAACGCTGCCCGAGATGCGCCGCGTGCGGCTGCTGGAGATGG
3961  CGGACGCGATGGATATGTTCTGCCAAGGGTTGGTTTGCGCATTCACAGTTCTCCGCAAGA
4021  ATTGATTGGCTCCAATTCTTGGAGTGGTGAATCCGTTAGCGAGGTGCCGCCGGCTTCCAT
4081  TCAGGTCGAGGTGGCCCGGCTCCATGCACCGCGACGCAACGCGGGGAGGCAGACAAGGTA
4141  TAGGGCGGCGCCTACAATCCATGCCAACCCGTTCCATGTGCTCGCCGAGGCGGCATAAAT
4201  CGCCGTGACGATCAGCGGTCCAGTGATCGAAGTTAGGCTGGTAAGAGCCGCGAGCGATCC
4261  TTGAAGCTGTCCCTGATGGTCGTCATCTACCTGCCTGGACAGCATGGCCTGCAACGCGGG
4321  CATCCCGATGCCGCCGGAAGCGAGAAGAATCATAATGGGGAAGGCCATCCAGCCTCGCGT
4381  CGCGAACGCCAGCAAGACGTAGCCCAGCGCGTCGGCCGCCATGCCGGCGATAATGGCCTG
4441  CTTCTCGCCGAAACGTTTGGTGGCGGGACCAGTGACGAAGGCTTGAGCGAGGGCGTGCAA
4501  GATTCCGAATACCGCAAGCGACAGGCCGATCATCGTCGCGCTCCAGCGAAAGCGGTCCTC
4561  GCCGAAAATGACCCAGAGCGCTGCCGGCACCTGTCCTACGAGTTGCATGATAAAGAAGAC
4621  AGTCATAAGTGCGGCGACGATAGTCATGCCCCGCGCCCACCGGAAGGAGCTGACTGGGTT
4681  GAAGGCTCTCAAGGGCATCGGTCGACGCTCTCCCTTATGCGACTCCTGCATTAGGAAGCA
4741  GCCCAGTAGTAGGTTGAGGCCGTTGAGCACCGCCGCCGCAAGGAATGGTGCATGCAAGGA
4801  GATGGCGCCCAACAGTCCCCCGGCCACGGGCCTGCCACCATACCCACGCCGAAACAAGC
4861  GCTCATGAGCCCGAAGTGGCGAGCCCGATCTTCCCCATCGGTGATGTCGGCGATATAGGC
4921  GCCAGCAACCGCACCTGTGGCGCCGGTGATGCCGGCCACGATGCGTCCGGCGTAGAGGAT
4981  CCGGAGCTTATCGACTGCACGGTGCACCAATGCTTCTGGCGTCAGGCAGCCATCGGAAGC
5041  TGTGGTATGGCTGTGCAGGTCGTAAATCACTGCATAATTCGTGTCGCTCAAGGCGCACTC
5101  CCGTTCTGGATAATGTTTTTTGCGCCGACATCATAACGGTTCTGGCAAATATTCTGAAAT
5161  GAGCTGTTGACAATTAATCATCGGCTCGTATAATGTGTGGAATTGTGAGCGGATAACAAT
5221  TTCACACAGGAAACAGAA   5238
```

FIG. 2.

```
   1 GCGCCCAATACGCAAACCGCCTCTCCCCGCGCGTTGGCCGATTCATTAATGCAGCTGGCA
  61 CGACAGGTTTCCCGACTGGAAAGCGGGCAGTGAGCGCAACGCAATTAATGTGAGTTAGCT
 121 CACTCATTAGGCACCCCAGGCTTTACACTTTATGCTTCCGGCTCGTATGTTGTGTGGAAT
 181 TGTGAGCGGATAACAATTTCACACAGGAAACAGCTATGACCATGATTACGAATTCCCGGG
 241 AAGTTCAAGGTGTGGAGTCTGGGGGAGGCTTAGTGAAGCCTGGAGGGTCCCTGAAACTCT
 301 CCTGTGCAGCCTCTGGATTCACTTTCAGTGACTATTACATGTATTGGGTTCGCCAGACTC
 361 CGGAAAAGAGGCTGGAGTGGGTCGCAACCATTAGTGATGGTGGTAGTTACACCTACTATC
 421 CAGACAGTGTGAAGGGGCGATTCACCATCTCCAGAGACAATGCCAAGAACAACCTGTACC
 481 TGCAAATGAGCAGTCTGAAGTCTGATGACACAGCCATGTATTACTGTGCAAGAGATAAGG
 541 CCTACTATGGTAACTACGGCGATGCTATGGACTACTGGGGTCAAGGAACCTCAGTCACCG
 601 TCTCCTCAGCCAAAACGACACCCCCATCTGTCTATCCACTGGCCCCTGGATCTGCTGCCC
 661 AAACTAACTCCATGGTGACCCTGGGATGCCTGGTCAAGGGCTATTTCCCTGAGCCAGTGA
 721 CAGTGACCTGGAACTCTGGATCCCTGTCCAGCGGTGTGCACACCTTCCCAGCTGTCCTGC
 781 AGTCTGACCTCTACACTCTGAGCAGCTCAGTGACTGTCCCCTCCAGCACCTGGCCCAGCG
 841 AGACCGTCACCTGCAACGTTGCCCACCCGGCCAGCAGCACCAAGGTGGACAAGAAAATTG
 901 TGCCCAGGGATTGTGGTTGATCAGTCGACCTGCAGCCAAGCTTGGCACTGGCCGTCGTTT
 961 TACAACGTCGTGACTGGGAAAACCCTGGCGTTACCCAACTTAATCGCCTTGCAGCACATC
1021 CCCCTTTCGCCAGCTGGCGTAATAGCGAAGAGGCCCGCACCGATCGCCCTTCCCAACAGT
1081 TGCGCAGCCTGAATGGCGAATGGCGCCTGATGCGGTATTTTCTCCTTACGCATCTGTGCG
1141 GTATTTCACACCGCATATGGTGCACTCTCAGTACAATCTGCTCTGATGCCGCATAGTTAA
1201 GCCAGCCCCGACACCCGCCAACACCCGCTGACGCGCCCTGACGGGCTTGTCTGCTCCCGG
1261 CATCCGCTTACAGACAAGCTGTGACCGTCTCCGGGAGCTGCATGTGTCAGAGGTTTTCAC
1321 CGTCATCACCGAAACGCGCGAGACGAAAGGGCCTCGTGATACGCCTATTTTTATAGGTTA
1381 ATGTCATGATAATAATGGTTTCTTAGACGTCAGGTGGCACTTTTCGGGGAAATGTGCGCG
1441 GAACCCCTATTTGTTTATTTTTCTAAATACATTCAAATATGTATCCGCTCATGAGACAAT
1501 AACCCTGATAAATGCTTCAATAATATTGAAAAAGGAAGAGTATGAGTATTCAACATTTCC
1561 GTGTCGCCCTTATTCCCTTTTTTGCGGCATTTTGCCTTCCTGTTTTTGCTCACCCAGAAA
1621 CGCTGGTGAAAGTAAAAGATGCTGAAGATCAGTTGGGTGCACGAGTGGGTTACATCGAAC
1681 TGGATCTCAACAGCGGTAAGATCCTTGAGAGTTTTCGCCCCGAAGAACGTTTTCCAATGA
1741 TGAGCACTTTTAAAGTTCTGCTATGTGGCGCGGTATTATCCCGTATTGACGCCGGGCAAG
1801 AGCAACTCGGTCGCCGCATACACTATTCTCAGAATGACTTGGTTGAGTACTCACCAGTCA
1861 CAGAAAAGCATCTTACGGATGGCATGACAGTAAGAGAATTATGCAGTGCTGCCATAACCA
1921 TGAGTGATAACACTGCGGCCAACTTACTTCTGACAACGATCGGAGGACCGAAGGAGCTAA
1981 CCGCTTTTTTGCACAACATGGGGGATCATGTAACTCGCCTTGATCGTTGGGAACCGGAGC
2041 TGAATGAAGCCATACCAAACGACGAGCGTGACACCACGATGCCTGTAGCAATGGCAACAA
2101 CGTTGCGCAAACTATTAACTGGCGAACTACTTACTCTAGCTTCCCGGCAACAATTAATAG
2161 ACTGGATGGAGGCGGATAAAGTTGCAGGACCACTTCTGCGCTCGGCCCTTCCGGCTGGCT
2221 GGTTTATTGCTGATAAATCTGGAGCCGGTGAGCGTGGGTCTCGCGGTATCATTGCAGCAC
2281 TGGGGCCAGATGGTAAGCCCTCCCGTATCGTAGTTATCTACACGACGGGGAGTCAGGCAA
2341 CTATGGATGAACGAAATAGACAGATCGCTGAGATAGGTGCCTCACTGATTAAGCATTGGT
2401 AACTGTCAGACCAAGTTTACTCATATATACTTTAGATTGATTTAAAACTTCATTTTTAAT
2461 TTAAAAGGATCTAGGTGAAGATCCTTTTGATAATCTCATGACCAAAATCCCTTAACGTG
2521 AGTTTTCGTTCCACTGAGCGTCAGACCCCGTAGAAAAGATCAAAGGATCTTCTTGAGATC
2581 CTTTTTTTCTGCGCGTAATCTGCTGCTTGCAAACAAAAAAACCACCGCTACCAGCGGTGG
2641 TTTGTTTGCCGGATCAAGAGCTACCAACTCTTTTTCCGAAGGTAACTGGCTTCAGCAGAG
2701 CGCAGATACCAAATACTGTCCTTCTAGTGTAGCCGTAGTTAGGCCACCACTTCAAGAACT
2761 CTGTAGCACCGCCTACATACCTCGCTCTGCTAATCCTGTTACCAGTGGCTGCTGCCAGTG
2821 GCGATAAGTCGTGTCTTACCGGGTTGGACTCAAGACGATAGTTACCGGATAAGGCGCAGC
2881 GGTCGGGCTGAACGGGGGGTTCGTGCACACAGCCCAGCTTGGAGCGAACGACCTACACCG
2941 AACTGAGATACCTACAGCGTGAGCTATGAGAAAGCGCCACGCTTCCCGAAGGGAGAAAGG
3001 CGGACAGGTATCCGGTAAGCGGCAGGGTCGGAACAGGAGAGCGCACGAGGGAGCTTCCAG
3061 GGGGAAACGCCTGGTATCTTTATAGTCCTGTCGGGTTTCGCCACCTCTGACTTGAGCGTC
3121 GATTTTTGTGATGCTCGTCAGGGGGCGGAGCCTATGGAAAAACGCCAGCAACGCGGCCT
3181 TTTTACGGTTCCTGGCCTTTTGCTGGCCTTTTGCTCACATGTTCTTTCCTGCGTTATCCC
3241 CTGATTCTGTGGATAACCGTATTACCGCCTTTGAGTGAGCTGATACCGCTCGCCGCAGCC
3301 GAACGACCGAGCGCAGCGAGTCAGTGAGCGAGGAAGCGGAAGA   3343
```

PROCESS FOR ACTIVATION OF RECOMBINANT PROTEIN PRODUCED BY PROKARYOTES

The present invention is concerned with a process for the activation of recombinant, biologically-active proteins expressed in prokaryotes.

The gene-technological production of proteins, for example antibodies, in heterologous host organisms leads to the formation of inactive, sparingly-soluble protein aggregates, i.e. so-called "inclusion bodies". It is assumed that the formation of such "inclusion bodies" is, inter alia, a result of the high protein concentrations in the cell arising following expression. In order to obtain biologically-active proteins, the inclusion bodies must be dissolved by renaturation and reduction and then the three-dimensional structure of the protein in its native spatial form again produced by the adjustment of suitable solution conditions (see M. Sela et al., Science, 125, 691/1957). The complete unfolding is achieved by the addition of high concentrations of chaotropic agents, for example urea or guanidine (R. Jaenicke, Prog. Biophys. Molec. Biol., 49, 117-237/1987). For the reduction of disulphide bridges, strong reducing agents, for example β-mercaptoethanol or 1,4-dithioerithritol are used.

However, when the renaturing the proteins from the denatured state, two competing reactions occur. Besides the desired folding into the native active state, aggregate formation is observed (see G. Zettlmeissl et al., Biochemistry, 18, 5567). In order to shift the equilibrium to the side of the native molecule, conditions are selected which, both, prevent the establishment of falsely folded and thus more unstable molecules and the non-specific exchange action thereof to aggregates and, does not hinder the refolding into the native state. This is achieved by the addition of chaotropic agents in labilizing concentrations. In addition, it must be observed that the protein concentration has a critical effect on the yield of renatured protein (see European Patent Specification No. 0,241,022). In the case of proteins which have dissulphide bridges in the native state, it is also necessary to provide redox conditions during the renaturing which make it possible to reduce falsely paired cystines producing protein molecules with correctly paired cysteins. So-called "oxido-shuffling solutions" of reduced and oxidised thiol reagent increase the yield of nativestructured and disulphide-bridged proteins.

That the renaturing of antibodies is possible after complete denaturing and reduction was shown for the first time by Haber using the example of a Fab fragment (see E. Haber, Biochemistry, 52, 1099-1106/1964). The yields amounted to 12 to 14%. These results were confirmed by the renaturing of a Fab fragment by Whitney and Tanford. They achieved yields of 8% (see P. L. Whitney and C. Tanford, Proc. Natl. Acad. Sci. USA, 53, 524/1965). A complete antibody was successfully renatured for the first time by Freedman and Sela, the yields being from 20 to 25% (see M. H. Freedman and M. Sela, J. Biol. Chem., 241, 2383-2396/1966; J. Biol. Chem., 241, 5225-5232/1966). It is to be noted that the native starting molecule was polyalanylated for the improvement of its solubility.

In the cited work, it is to be observed that the concern was with polyclonal antibodies or antibody fragments, i.e. a mixture of antibodies with different paratopes and different affinity constants. Since the heavy and light chains of this heterologous population associate purely statistically during of renaturation, renatured molecules are produced which do not agree with the native ones in terns of binding specificity and affinity.

As in the case of other eukaryotic proteins which have been cloned and expressed in Escherichia coli, heavy and light chains of antibodies expressed in Escherichia coli are also obtained in the form of insoluble "inclusion bodies" (see S. Cabilly et al., Proc. Natl. Acad. Sci. USA, 81, 3273-3277/1984; M. Y. Boss et at., Nucleic Acids Research, 12, 3791-3806/1984). For antibodies from transformed micro-organisms, processes were described by Cabilly et al. and Boss et al. which are said to make possible the renaturing of functional antibodies. However, for monoclonal antibodies, these processes only give yields of from about 0.2 to 5%.

Therefore, it is an object of the present invention to provide a process for the reactivation of biologically-active proteins expressed in prokaryotes in which the proteins obtained after expression in the form of "inclusion bodies" can be converted into their active renatured form in good yield.

Thus, according to the present invention, there is provided a process for the activation of recombinant biologically-active proteins expressed in prokaryotes by solubilization under denaturing and reducing conditions and subsequent reactivation under oxidising and renaturing conditions, wherein working is carried out at a protein concentration of from 1 to 1000 μg./ml. and, between the solubilization and the reactivation, dialysis is carried out against a buffer with a pH value of from 1 to 4 containing 4 to 8 mole/liter guanidine hydrochloride or 6 to 10 mole/liter urea.

Surprisingly, we have ascertained that after dialysis in the presence of urea or, especially in the presence of guanidine hydrochloride, extraordinarily high yields of active protein are obtained after the reactivation.

The present invention is suitable for use in connection with all recombinant proteins produced in prokaryotes. In particular production of antibodies and fragments thereof and for t-PA and t-PA-like proteins and derivatives thereof can be enhanced.

In a preferred embodiment of the present invention, the dialysis buffer contains 5 to 7 mole/liter of guanidine hydrochloride.

It is preferred to work at a pH value of from 9 to 12, when reactivating the proteins together with a GSH (reduced glutathione) concentration of 0.1 to 20 mmole/liter, a GSSG (glutathione disulfide) concentration of 0.01 to 3 mmole/liter and with a non-denaturing concentration of the denaturing agent. The reactivation is carried out over a period of from 1 to 300 hours. In an especially preferred embodiment, the GSH concentration is from 0.2 to 10 mmole/liter and/or the GSSG concentration of from 0.05 to 1 mmole/liter.

In another preferred embodiment of the present invention, in the reactivation stage, the thiol groups of the antibody are first converted into mixed disulphides of antibody and glutathione, via adding GSSG under denaturing conditions followed by dialysis against the buffer containing guanidine hydrochloride or urea and then reactivated at a pH value of from 6 to 10, using a GSH concentration of 0.1 to 5 mmole/liter and a non-denaturing concentration of a denaturing agent over a period of time of from 1 to 300 hours.

As denaturing agent, as a rule, a denaturing agent conventionally employed for the activation of proteins under oxidizing conditions or arginine can be used. Preferably, the agent used is arginine guanidine hydrochloride and/or at least one compound of the general formula:

$$R_2—CO—NRR_1 \quad (I)$$

wherein R and $R_1$ are hydrogen atoms or alkyl radicals containing from 1 to 4 carbon atoms and $R_2$ is a hydrogen atom or $—NRR_1$ or an alkyl radical containing from 1 to 3 carbon atoms. These denaturing agents can also be used in the form of mixtures. The concentration of arginine and/or guanidine hydrochloride is preferably from 0.1 to 1.0 mole/liter and an especially preferred concentration is from 0.25 to 0.8 mole/liter. The concentration of the compound of general formula I is preferably from 0.5 to 4 mole/liter and a especially preferred concentration is from 1 to 3.5 mole/liter.

In a further preferred embodiment of the present invention, the reactivation step is carried out in the presence of a foreign protein. As such, can be used any foreign protein as long as it is not proteolytically-active. It is preferred to use bovine serum albumin (BSA), for example in an amount of from 1 to 3 mg./ml. The addition of BSA brings about a slight increase of the yield and a stabilization of the protein, probably by protection against surface denaturing and/or proteolytic breakdown.

The usual process conditions correspond to the conditions known and usual for reactivation steps. Reactivation is advantageously carried out at a temperature from about 5° C. to 30° C. and preferably at about 10° C. The process steps preceding and following the dialysis and reactivation step (reoxidation/activation), such as cell digestion, solubilization (solubilization, reduction), can be carried out by the methods known from the prior art as taught, for example in European Patent Specifications Nos. A-0,114,506 and A-0,093,619, for the reactivation of heterologously expressed proteins or of t-PA. However, for a result which is optimum with regard to yield and activation, it is advantageous to carry out individual or all process steps using the protocols as follows explained.

Cell digestion can be carried out by usual methods usual for this purpose, for example by means of ultrasonics, high pressure dispersion or lysozyme digestion can be used. Preferably, the digestion is carried out in a buffer solution appropriate for the adjustment of a neutral to weakly acidic pH value as suspension medium, for example in 0.1 mole/liter Tris/HCl. After the cell digestion, the insoluble components (inclusion bodies) are separated off in any desired way, preferably by centrifuging or filtration. After washing with agents which do not disturb the proteins but which dissolve foreign proteins as far as possible. The washing agent may be for example, water or a phosphate buffer, either of which may contain mild detergents, such as Triton. Following washing, the precipitate or pellet is subjected to solubilization (solubilization/reduction).

Solubilization preferably takes place in the alkaline pH range and especially at pH 8.6±0.4 and in the presence of a reducing agent of the mercaptan group and of a denaturing agent.

As denaturing agents, those which are known from the prior art, for example European Patent Specification No. A-0,114,506 can be used, especially preferred are guanidine hydrochloride or compound of general formula I. Especially preferred is a concentration of guanidine hydrochloride of 6 mole/liter or a concentration of the compound of general formula I of 8 mole/liter.

As reducing agent from the mercaptan group, there reduced glutathione (GSH) e.g., can be used or 2-mercaptoethanol, for example in a concentration of about 50 to 400 mole/liter and/or especially dithioerythritol (DTE) or dithiothreitol (DTT), for example in a concentration of about 80 to 400 mmole/liter., or cysteine. Solubilization advantageously takes place at ambient temperature for a period of from 0.5 to several hours. Preferably, this incubation is and for 2 hours. For the prevention of oxidation of the reducing agent by atmospheric oxygen, it can be advantageous to added EDTA thereto, preferably in an amount of 1 to 10 mmole/liter. Besides the solubilization reduction, the solubilization step also has a purifying effect since the greater part of the foreign proteins does not go into solution.

Another embodiment of the present invention depends upon the formation between the mixed disulphides of biologically-active proteins expressed in prokaryotes and glutathione before the reactivation step. For the formation of these mixed disulphides of protein and glutathione, the dialysed and reduced proteins which have been separated from reducing agents are incubated with a denaturing agent-containing dilute solution of GSSG, at for example a concentration of 0.2 mole/liter. Activation takes place after separating the oxidation agent by renewed dialysis against the guanidine hydrochloride- or urea-containing buffer at a pH value of from 6 to 10, with a GSH concentration of 0.1 to 5 mmole/liter and with a non-denaturing concentration of a denaturing agent over a period of time of from 1 to 300 hours.

In all other reaction steps, the activation of the protein via the formation of the mixed disulphides with GSSG corresponds to the embodiments for the activation of proteins of the previously described part of the present invention. In the case of this embodiment, the pH optimum is from 6 to 8 and the activated proteins are stable for a comparatively long period of time in the renaturing buffer.

According to the present invention, it is possible, for example, to reactivate as antibodies as which have been expressed in prokaryotes with a yield of up to 30% with reference to their immune reactivity. This corresponds to an increase of about 10 fold compared to processes known from the prior art. "Antibodies", as used herein includes whole antibodies, as well as all known fragments thereof.

The following Examples are given for the purpose of illustrating the present invention, with reference to the accompanying drawings. If not stated otherwise, the statements of percentage are percentages by weight.

BRIEF DESCRIPTION OF THE FIGURES

FIG. 1 shows the sequence of plasmid pBT111 for the expression of the kappa chain of MAB 33 (nucleotide positions 7 to 663); and FIG. 2 shows the DNA sequence of plasmid p10169 for the expression of the Fd chain of MAB 33 (nucleotide positions 240 to 917).

DESCRIPTION OF PREFERRED EMBODIMENTS

Example 1

Expression of antibody fragments in *Escherichia coli*. 1.1. Construction of a plasmid for the expression of the MAB 33 kappa chain in *Escherichia coli*.

The cloning of kappa chain cDNA for MAB 33 as Pst I fragment in pBR 322 has been described (see P. Buckel et al., Gene, 51, 13–19/1987). With the restriction endonuclease Mnl I, the cDNA was cleaved nucleotide-neighbouring the first amino acid codon of the mature kappa chain. This cDNA was cloned with the help of an adapter (5'CATG3' hybridized with 5'CATGAATT3') as an Eco RI-Pst I fragment into the vector pKK 223-3, DSM 3694P, which had also been cleaved with Eco RI and Pst I (see Brosius et al., Plasmid, 6, 112–118/1981). For shortening the 3'-untranslated region of the cDNA, the resulting plasmid was cleaved with Pst I, shortened nucleolytically with Bal 31 and subsequently the Eco RI-Bal 31 fragment corresponding to the kappa chain cDNA was cloned back into the vector with the help of a Hind III linker. The resulting plasmid is designated as pBT 111 (FIG. 1 of the accompanying drawings shows the sequence of the expression plasmid; kappa chain runs from nucleotide position 7 to 663).

1.2. Construction of a plasmid for the expression of the Fc Fd fragment of the gamma chain of MAB 33 in *E. coli*

The cloning of the MAB 33 gamma chain cDNA as a Pst I fragment into pBR 322 has also been described (see Buckel et al., v. supra, 1987). For the expression, immediately before the first amino acid of the mature gamma chain an Xma I cleavage position was introduced by means of oligonucleotide-directed mutagenesis. A gamma Fc fragment was produced by the introduction of a stop codon after amino acid position 225 by means of the same technique, in which case Bcl I and a Sal I cleavage position were also introduced. The resulting Xma I-Sal I fragment, which codes for the gamma Fc fragment, was cloned into pUC8 (see Vieira and Messing, Gene, 19, 259–268/1982). FIG. 2 of the accompanying drawings shows the sequence of the resulting expression plasmid p10169 (gamma Fc from nucleotide positions 240 to 917).

1.3 Expression of antibody chains in *E. coli*

The expression plasmids pBT111 and p10169 were each transformed individually into *Escherichia coli* (DSM 3689) which also contained a plasmid for the expression of the lac repressor (lac I$^q$) in trans. The *Escherichia coli* cells were cultured in LB medium up to an optical density of $OD_{550\ nm}=0.5$, then induced with 1 g./liter isopropyl-β-D-thiogalactoside (IPTG) and incubated for a further 4 hours at 37° C. Subsequently, the cells were centrifuged off.

1.4 Preparation of the "inclusion bodies"

For this purpose, there were taken, per immunoglobulin chain, about 25 g. *Escherichia coli* (cf. Example 1.3) Moist cell mass in 580 ml. 0.1 mole/liter Tris/HCl (pH 6.5) and 20 mmole/liter EDTA and the cells homogenized with a shearing rod (Ultraturax). Lysozyme at 0.25 mg./ml. was added, followed by incubation for 30 minutes at ambient temperature. This was subsequently suspended in 0.5 mole/liter aqueous sodium chloride solution containing 5% v/v Triton X-100 and homogenized with a shearing rod (Ultraturax) and further stirred for 30 minutes at ambient temperature. Thereafter, centrifugation was carried out in a Sorvall GSA rotor for 50 minutes at 4° C. and 13000 r.p.m. The pellets were taken up in 300 ml. 0.1 mole/liter Tris/HCl (pH 6.5), 20 mmole/liter EDTA and 2.5% v/v Triton X-100 and homogenized. Further centrifugation was then carried out for 30 minutes at 4° C. and 13000 r.p.m., again in a Sorvall GSA rotor. The pellets were taken up in 300 ml. 0.1 mole/liter Tris/HCl (pH 6.5), 20 mmole/liter EDTA and 0.5% v/v Triton X-100 and homogenized. Thereafter, there were two further centrifugations were carried out, each for 30 minutes at 4° C. at 13000 r.p.m., in a Sorvall GSA rotor and in each case thereafter the pellets were taken up in 300 ml. and 250 ml., respectively, of 0.1 mole/liter Tris/HCl (pH 6.5) and 20 mmole/liter EDTA and homogenised.

Example 2

Denaturing of the antibody

Lyophilisates of antibody MAB 33 obtained from hybridoma cells lines (ECACC 88091404) or Fab fragments thereof (for the production of Fab fragments, cf. A. Johnstone and R. Thorpe in Immunochemistry in Practice, pub. Blackwell Scientific Publications, 1982, pp. 52–53), as well as the pellets of the "inclusion bodies" prepared according to Example 1, were incubated in 0.1 mole/liter Tris. HCl (pH 8.5), 6 mole/liter guanidine hydrochloride, 2 mmole/liter EDTA and 0.3 mole/liter DTE for 3 hours at ambient temperature. The protein concentration was from 4 to 6 mg./ml. Chain separation was examined with SDS-PAGE under non-reducing conditions. The complete reduction of the disulphide bridges was confirmed by the determination of the free SH groups according to the method of G. L. Ellmann (Arch. Biochem. Biophys., 82, 70/1959). Subsequently, the solutions were adjusted to pH 3 with concentrated hydrochloric acid.

The Examples given in the following for renaturation were carried out, as described in Example 2, with completely denatured, reduced MAB 33 or MAB 33 Fab or the antibody chains from the "inclusion bodies" in 1:100 dilution in reoxidation buffer after dialysis against 6 mole/liter guanidine hydrochloride (pH 2). The renaturing batches were thermostated at 20° C.

Example 3

Renaturing of MAB 33 Fab fragments.

The reoxidation buffer contained 0.1 mole/liter Tris. HCl (pH 8.5), 0.5 mole/liter L-arginine and 2 mmole/liter EDTA.

The protein concentration ranged from 30 to 60 μg./ml. The period for renaturation was up to 200 hours. The reoxidation was examined with the conformation-specific ELISA test system (see Example 8) for passive immunoreactivity.

The following Tables 1A to 1C show the yield of active MAB 33 Fab fragment depending upon the variation of:

1A the DTE concentration in the case of constant GSSG concentration (5 mmole/liter GSSG);
1B the GSSG concentration in the case of constant DTE concentration (3 mmole/liter DTE);
1C the GSSG concentration in the case of constant GSH concentration (1 mmole/liter).

TABLE 1A

| DTE (mmole/liter) | yield (%) |
| --- | --- |
| 0 | 53 |
| 1 | 53 |
| 3 | 41 |
| 5 | 8 |
| 10 | 3 |

TABLE 1B

| GSSG (mmole/liter) | yield (%) |
| --- | --- |
| 0 | 18 |
| 1 | 15 |
| 3 | 23 |
| 5 | 32 |
| 10 | 37 |

TABLE 1C

| GSSG (mmole/liter) | yield (%) |
| --- | --- |
| 0 | 22 |
| 0.1 | 53 |
| 1 | 38 |
| 5 | 28 |

Example 4

Completely denatured, reduced MAB 33 Fab fragments were dialysed against 6 mole/liter guanidine hydrochloride (pH 2) and subsequently reoxidised in 0.1 mole/liter Tris. HCl (pH 8.5), 0.3 mole/liter guanidine hydrochloride, 0.2 mole/liter GSSG, 2 mmole/liter GSH and 2 mmole/liter EDTA at a temperature of 20° C. and a period of renaturing of about 200 hours. The following Table 2 shows the yield of active MAB 33 Fab depending upon the variation of the protein concentration in the case of the renaturing. The reoxidation was examined with the Elisa test system for active immunoreactivity (see Example 8).

TABLE 2

| Fab concentration (μg./ml.) | yield (%) |
| --- | --- |
| 5 | 13 |
| 10 | 9 |
| 20 | 4 |
| 30 | 3 |
| 70 | 1 |
| 130 | 0.5 |
| 660 | 0 |

Example 5

Completely denatured, reduced MAB 33 antibodies were dialysed against 6 mole/liter guanidine hydrochloride (pH 2) and were subsequently reoxidized in 0.1 mole/liter Tris.HCl (pH 8.5), 0.5 mole/liter L-arginine, 2 mmole/liter EDTA and 1 mmole/liter GSH at a temperature of 20° C. and a period of renaturing of about 200 hours. Reoxidation was examined with the Elisa test system (see Example 8) for active immunoreactivity. The following Table 3 shows the yield of active antibody depending upon the variation of the GSSG concentration at constant GSH concentration (1 mmole/liter).

TABLE 3

| GSSG (mmole/liter) | yield (%) |
| --- | --- |
| 0 | 2.0 |
| 0.1 | 3.5 |

TABLE 3-continued

| GSSG (mmole/liter) | yield (%) |
| --- | --- |
| 0.5 | 4.7 |
| 1 | 4.8 |
| 2 | 4.2 |
| 4 | 3.9 |
| 6 | 3.4 |
| 10 | 2.7 |

Example 6

Renaturing after derivatisation to the mixed disulphide.

The denaturing of MAB 33 or MAB 33 Fab was carried out as described in Example 2. Dialysis against 6 mole/liter guanidine hydrochloride followed (pH 2) and subsequently derivatisation with 6 mole/liter guanidine hydrochloride, 0.2 mole/liter GSSG and 0.1 mole/liter Tris.HCl (pH 8.5) at ambient temperature over a period of time of about 5 hours took place. After renewed dialysis against 6 mole/liter guanidine hydrochloride (pH 2), the renaturing was carried out in different variants.

Table 4A shows the renaturing of MAB 33 Fab in 0.1 mole/liter Tris.HCl (pH 7), 0.5 mole/liter L-arginine and 2 mmole/liter EDTA at 20° C. over a period of about 200 hours. The renaturing was tested with the conformation-specific Elisa test system for passive (see Example 8) immunoreactivity depending upon the GSH concentration.

Table 4B shows the yield of active MAB 33 Fab in the above buffer with 2 mmole/liter GSH depending upon the pH of the buffer.

Table 5A shows the renaturing of MAB 33 IgG in 0.1 mole/liter Tris.HCl (pH 7.0), 0.5 mole/liter L-arginine and 2 mmole/liter EDTA at a temperature of 20° C. over a period of renaturing of about 200 hours depending upon the GSH concentration. The renaturing was examined with the conformation-specific Elisa Test system for passive immunoreactivity (see Example 8).

Table 5B shows the yield of active antibody in the above buffer with 2 mmole/liter GSH depending upon the pH value.

TABLE 4A

| GSH (mmole/liter) | yield (%) |
| --- | --- |
| 0 | 5 |
| 0.1 | 48 |
| 0.5 | 48 |
| 1 | 41 |
| 2 | 36 |
| 3 | 31 |
| 4 | 27 |
| 7 | 24 |
| 10 | 23 |

TABLE 4B

| pH | yield (%) |
| --- | --- |
| 7 | 40 |
| 8 | 39 |
| 9 | 30 |
| 10 | 19 |
| 11 | 1 |

TABLE 5A

| GSH (mmole/liter) | yield (%) |
| --- | --- |
| 0 | 0.3 |

TABLE 5A-continued

| GSH (mmole/liter) | yield (%) |
| --- | --- |
| 0.1 | 3.0 |
| 0.2 | 4.0 |
| 0.5 | 3.8 |
| 1 | 3.1 |
| 2 | 2.5 |
| 3 | 2.0 |
| 6 | 1.4 |
| 10 | 1.4 |

TABLE 4B

| pH | yield (%) |
| --- | --- |
| 6 | 3.9 |
| 7 | 3.8 |
| 8 | 2.9 |
| 9 | 1.5 |
| 10 | 0.8 |
| 11 | 0.6 |

Example 7

Renaturing of antibody chains expressed in *Escherichia coli*.

Inclusion bodies of the complementary single chain (kappa and Fd, Example 1) were solubilized as described in Example 2. Subsequently, dialysis was carried out against 6 mole/liter guanidine hydrochloride (pH 2). Solubilization and dialysis took place separately for both chains.

For the reoxidation, equimolar amounts of the reduced single chains were simultaneously diluted in a 100 fold volume of 0.1 mole/liter Tris-HCl (pH 8.5), 0.6 mole/liter L-arginine, 0.1 mmole/liter GSSG, 1 mmole/liter GSH and 2 mmole/liter EDTA. Renaturing took place by incubation over a period of 200 hours at 20° C.

The yield of native, biologically-active protein amounted to 18%. The proportion of native antibodies was determined by measurement of the passive immunoreactivity (see Example 8).

Example 8

Detection of passive and active immunoreactivity, as well as inhibiting activity

8.1. Detection of the passive immunoreactivity of the monoclonal antibody against human CK-MM (skeletal muscle isoenzyme of human creatine kinase)

By passive immunoreactivity is here to be understood the formation of native-structured epitopes on the native or renatured antibodies. The detection of these epitopes takes place by conformation-specific antimouse antibodies, which have been obtained from another type of animal (here sheep), in an Elisa test system.

Preparation of conformation-specific, polyclonal sheep anti-mouse Fab antibodies.

Antiserum against polyclonal mouse immunoglobulin was prepared in sheep according to the procedure of A. Johnstone and R. Thorpe, Immunochemistry in Practice, pub. Blackwell Scientific Publications, Oxford, 1982, pp. 27–31.

The IgG fraction of the antiserum was isolated according to Johnstone and Thorpe (loc. cit., pp. 44–46) by ammonium sulphate fractionation and DEAE-ion exchange chromatography.

500 mg. of this IgG fraction were adsorbed on 20 ml. of a mouse kappa chain Spherosil immunoadsorber (1.5 mg. mouse kappa chain/ml. Spherosil) until anti-mouse kappa activity was no longer detectable by an enzyme immune test. The IgG fraction was then passed over a column with 20 ml. of a mouse Fab Spherosil filling (5 mg. mouse Fab/ml. Spherosil) and the specifically adsorbed portion of the IgG fraction eluted with 0.2 mole/liter glycine (pH 2.8). After dialysis against 1 mmole/liter acetic acid, this fraction was lyophilized.

By means of immune tests, it was ascertained that the so produced IgG did not react with free M-kappa, M-gamma and M-Fd chains or with incompletely folded M-kappa/M-Fd complexes. Binding takes place with M-Fab, M-IgG and completely folded complexes of M-kappa/M-Fd and M-kappa/M-gamma.

Renatured antibodies and native standard samples were pre-incubated with conformation-specific antimouse Fab antibodies. Depending upon the number of native formed conformation epitopes, differing numbers of binding positions of the conformation-specific antimouse Fab antibody were saturated. The pre-incubation solution was introduced into test tubes, together with murine antibody-enzyme conjugate (antibody-peroxidase conjugate), the walls of the test tubes being coated with mouse antibodies.

The unsaturated conformation-specific anti-mouse antibodies from sheep then bridged the wall-bound mouse antibodies with the mouse antibody-enzyme conjugates, the amount of bound conjugate there being indirectly proportional to the amount of native or renatured antibodies in the pre-incubation solution. The spectroscopic detection took place, after reaction of the chromogenic substrate ABTS® (2,2'-azino-bis-(3-ethylbenzothiazoline-6-sulphonate) by the antibody-conjugated enzyme, by absorption measurement at 405 nm (see H. U. Bergmeyer, Methods in Enzymology, 3rd edition, Volume 9, pp. 15–37).

8.2. Detection of the active immunoreactivity of the monoclonal antibody

MAB 33 IgG specifically recognises the skeletal muscle isoenzyme of human creatine kinase (CK-MM; cf. P. Buckel et al., Gene, 51, 13–19/1987).

By active immunoreactivity is here to be understood the reaction of the native or regenerated antibody with the specific antigen (in the present case, human CK-MM).

In an Elisa test system, this reaction was colorimetrically quantitatively determined quantitatively with the help of enzyme-conjugated, polyclonal anti-mouse antibodies via the reaction of the chromogenic substrate ABTS.

8.3. Detection of the inhibition activity of the monoclonal antibodies

MAB 33 IgG recognises an epitope which is only formed on the M subunits of the skeletal muscle-specific isoenzyme CK-MM. By binding to the epitope, the enzymatic activity is inhibited by 80% (see P. Buckel et al., 1987). The CK-MM inhibition test is thus a very conclusive test for the detection of the reconstitution of MAB 33 after complete denaturing and reduction since only a completely renatured antigen binding position can inhibit the enzyme.

The activity of the creatine kinase was determined with the help of a coupled enzymatic test of Boehringer Mannheim GmbH (see H. U. Bergmeyer, Methods of Enzymatic Analysis, 3rd edition Volume III, pp 510-540). Creatine kinase thereby reacts with creatine phosphate and ADP to give creatine and ATP. In order to obtain a spectroscopically detectable reaction, the resultant ATP is utilized by hexokinase for the phosphorylation of glucose to give glucose-6-phosphate. Glucose-6-phosphate is oxidized by glucose-6-phosphate dehydrogenase with the formation of $NADPH+H^+$ from $NADP^+$ to give gluconate-6-phosphate. The activity of the creatine kinase can be calculated from the change of extinction per minute.

From a calibration curve with native antibody against CK-MM, the amount of native material which corresponds to the inhibition action in the renatured batch can be determined. The proportion of inhibition-active protein, referred to the total amount of protein in the renaturing batch, gives the percentage yield of inhibition-active antibodies.

8.4. Comparative determination of the renaturing yield by means of passive/active immunoreactivity and inhibition activity Completely denatured, reduced MAB 33 Fab fragments were dialysed against 6 mole/liter guanidine hydrochloride (pH 2) and subsequently reoxidised by 1:100 dilution in 0.1 mole/liter Tris-HCl (pH 8.5), 0.5 mole/liter L-arginine, 0.2 mmole/liter GSSG, 2 mmole/liter GSH and 2 mmole/liter EDTA at a temperature of 20° C. and a period of renaturing of about 200 hours.

On the basis of the relatively high antibody concentration which must be used in the case of the measurement of the inhibition activity, the renaturing batch was concentrated. For this purpose, the renatured solution was dialysed against 1 mmole/liter acetic acid and subsequently lyophilised. The lyophilisate was taken up in water (water:renaturing volume=1:200) and dialysed against 50 mmole/liter potassium phosphate, 0.15 mole/liter sodium chloride (pH 7.5).

The following Table 6 shows the yield of active Fab fragment in the dialysate, determined by passive-active immunoreactivity and inhibition activity.

TABLE 6

| test method | yield (%) |
| --- | --- |
| passive immunoreactivity | 28 |
| active immunoreactivity | 26 |
| inhibition activity | 25 |

Example 9

Activation of t-PA from *Escherichia coli*

As described in Example 1.4, "inclusion bodies" are prepared as pellets from moist cell mass of *Escherichia coli*, DSM 3689, transformed with pePa 133 (see European Patent Specification No. 0,242,835). The pellets of the "inclusion body" preparation were incubated in 0.1 mole/liter Tris-HCl (pH 8.5); 6 mole/liter guanidine hydrochloride; 2 mmole/liter EDTA and 0.3 mole/liter DTE for 3 hours at ambient temperature at a protein concentration of from 4 to 6 mg./ml. Subsequent to the solubilisation, the pH of the solution was adjusted to pH 3 with concentrated hydrochloric acid. The reducing agent and buffer components were separated off by dialysis against 6 mole/liter guanidine hydrochloride (pH 2) at 4° C.

Renaturing of t-PA

Renaturing of the so obtained denatured, reduced protein took place by dilution with 0.1 mole/liter Tris-HCl (pH 10.5), 0.5 mole/liter L-arginine, 1 mmole/liter EDTA and 1 mg./ml. bovine serum albumin. The protein concentration was from 10 to 30 μg./ml., the temperature 20° C. and the period of renaturing 24 hours.

The reactivation was determined according to the test procedure for t-PA standard of Boehringer Mannheim GmbH, Order No. 1080954. The following Tables 7A and 7B show the yield of active t-PA depending upon the variations of 7A the GSSG concentration at constant DTE concentration (3 mmole/liter); and 7B the GSSG concentration at constant GSH concentration (1 mmole/litre).

TABLE 7A

| GSSG (mmole/liter) | yield (%) |
| --- | --- |
| 0 | 0 |
| 1 | 1 |
| 3 | 7 |
| 5 | 12 |
| 10 | 6 |

TABLE 7B

| GSSG (mmole/liter) | yield (%) |
| --- | --- |
| 0 | 6 |
| 0.1 | 14 |
| 1 | 10 |
| 5 | 1 |

Example 10

Renaturing of tPA derivative "K2P"

Cells of *E. coli* DSM 2093 were transformed with plasmids pA27fd and pUBS500, which are now described, as is the transformation protocol and the resulting product.

First, the plasmid pA27fd was made. This involves several steps, which are now described.

a. Preparation of Plasmid pA27.3

This plasmid was made from starting plasmid pREM7685, described in EPA 0 242 836, which contains a tac-promotor, a lacoperator region with ATG start codon, the region coding for t-PA derivative FK2p (i.e., nucleotides 190-336, (F domain) 715-1809 (K2 domain, P domain, small portion of 3'UT), the transcription terminator of plasmid pKK223-3, a β-lactamase gene, a kanamycin resistance gene, and the ori of plasmid pACY177. The above nucleotide sequences are according to Pennica et al., Nature 301: 214-221 (1983).

The F-domain of FK2P in pREM7685 was deleted essentially following Morinaga et al., Biotechnology 21:634 (1984). Two fragments were isolated from pREM7685 for heteroduplex formation. Fragment A was cleaved with EcoRI, and the cleavage products were separated by gel electrophoresis and the largest EcoRI fragment was eluted from the gel. Fragment B: plasmid pREM7685 was linearized with the restriction enzyme KhoI. The linearized plasmid was also obtained preparatively by gel electrophoresis. The following oligonucleotide was prepared synthetically for the mutagenesis.

5'TG TCT TAC CAA GGA AAC AGT GA 3'

In order to form the heteroduplex, fragment A, fragment B (450 fmol of each) and the oligonucleotide (75 pmol) were mixed and incubated initially for 3 minutes at 100° C. in the presence of 50 mmol/l NaCl, 10 mmol/l Tris-HCl, pH 7.5 and 10 mmol/l MgSO$_4$ and then transferred immediately onto ice. The renaturation of the DNA was carried out for 30 minutes at 60° C. The following were added to the heteroduplex for repair synthesis.

Deoxynucleotide triphosphate (0.25 mmol/l), ATP (1 mmol/l), NaCl (100 mmol/l), Tris-HCl, pH 7.5 (6.5 mmol/l), MgCl$_2$ (8 mmol/l), β-mercaptoethanol (1 mmol/l), Klenow-fragment of the DNA-polymerase from E. coli (0.125 U/µl reaction mixture) and T4-ligase (0.1 U/µl reaction mixture). The repair synthesis was carried out for 4 hours at 16° C. Subsequently, this preparation was transformed into *E. coli* cells (RM82, DSM 3689) with a lac I$^q$-plasmid and the transformed cells were selected by the addition of 25 µg/ml kanamycin to the culture medium.

Those clones which contain the plasmid pA27.3 which encode the t-PA derivative K2P according to the present invention were selected by the colony hybridization technique using the mutagenesis oligonucleotide described above as a probe. This plasmid differs from the starting plasmid pREM7685 inter alia by the absence of a PstI or a SspI cleavage site. Both these cleavage sites are contained in the region of the starting plasmid which codes for the F-domain.

b. Production of plasmid pA27fd

Plasmid pA27.3 described supra was used in connection with other plasmids to make pA27fd. This was done to increase the yield of expression product.

The plasmid pKK223-3 (DSM 3694P) was split and DNA coding for tPA was inserted therein. This generated plasmid pePA 126.1.

Following generation of pePA 126.1, an fd-terminator sequence was first integrated into this plasmid. For this, the plasmid pePA 126.1 was linearized with the restriction enzyme Hind III. The plasmid cleaved in this manner was separated by gel electrophoresis and isolated preparatively. The plasmid pLBU1 (Beck et al., (1978), Nucl. Acids. Res., 5, 4495-4503; Gentz et al., (1981) PNAS 78 (8): 4963) was cleaved with Hind III and a Hind III fragment of about 360 bp which contained the fd-terminator was isolated preparatively by gel electrophoresis and gel elution. The linearized plasmid pePA 126.1 and the 360 bp Hind III fragment from pLBU1 were ligated. The ligation preparation was co-transformed with the plasmid pUBS 500, in *E. coli*, DMS 2102. From the clones, those were selected that contained the desired plasmid pePA 126 fd which differs from the starting plasmid pePA 126.1 in that it contains a second Hind III cleavage site.

Two fragments were isolated from the plasmid pePA 126 fd: a BamHI/PvuI-fragment of 3.4 kb size and a PvuI/XmaI fragment of 1.3 kb size. Both these fragments were ligated with a BamHI/XmaI fragment of about 1.3 kb from plasmid pA27.3 and transformed with the plasmid pUBS 500 into *E. coli*. The resultant plasmid was named pA27 fd and can be distinguished from pePA 126 fd in that in a restriction digest with EcoRI the second smallest EcoRI fragment from pePA 126 fd of about 610 bp length is about 515 bp shorter in pA27 fd.

c. Production of the K2P derivative

Cells of *E. coli* DSM 2093 were then transformed with plasmids pA27fd, which codes for K2P, and pUBS 500, cultured, and the cell mass recovered. Denatured, reduced K2P was obtained from this cell mass, following Example 9.

The solution of the denatured, reduced protein in 6 mole/liter guanidine hydrochloride (pH 2) was adjusted with GSSG to 0.1 mole/liter and with Tris to 0.1 mole/liter. Subsequently, the pH value was adjusted to 8.5 with sodium hydroxide. After incubating for 2 hours at ambient temperature, the oxidation agent and the buffer components were separated off by renewed dialysis against 6 mole/liter guanidine hydrochloride (pH 2) at 4° C.

The renaturing of the denatured, oxidised protein ("mixed disulphide") took place after dilution in renaturing buffer. The protein concentration ranged from 30 to 60 µg./ml, the temperature 20° C. and the period of renaturing 12 hours.

The following Table 8A shows the reactivation of K2P in 0.1 mole/liter Tris-HCl (pH 8.5), 0.8 mole/liter L-arginine and 2 mmole/liter EDTA depending upon the GSH concentration and the following Table 8B shows the yield of active K2P in the above buffer with 0.5 mmole/liter GSH depending upon the pH value of the buffer.

TABLE 8A

| GSH (mmole/liter) | yield (%) |
|---|---|
| 0 | 0 |
| 0.1 | 14 |
| 0.5 | 26 |
| 1 | 20 |
| 2 | 10 |

TABLE 8B

| pH | yield (%) |
|---|---|
| 7 | 6 |
| 8 | 15 |
| 9 | 23 |
| 10 | 7 |

We claim:
1. Method for activating a protein produced in insoluble, inactive form by expression of a gene in a prokaryote, comprising:
   (i) digesting a cell sample of said prokaryote which contains the protein in insoluble, inactive form,
   (ii) recovering the insoluble, inactive protein,
   (iii) solubilizing the insoluble, inactive protein under conditions favoring denaturing and reduction of said insoluble, inactive protein to form a solubilized protein,
   (iv) dialyzing the solubilized protein against a buffer at a pH of from 1 to 4 which contains from 4 to 8 moles/liter guanidine chloride or from 6 to 10 moles/liter urea, and
   (v) treating a solution containing said solubilized protein at a concentration of from 1 to 1000 ug/ml under conditions favoring oxidation and renaturation thereof so as to activate it.

2. Method of claim 1, wherein said dialysis buffer contains guanidine hydrochloride in an amount ranging from 5 to 7 moles/liter.

3. Method of claim 1, comprising reactivating said deactivated protein at a pH value of from 9 to 12 in the presence of reduced glutathione (GSH) at a concentration of from 0.1 to 20 mmole/liter and of glutathione disulphide (GSSG) at a concentration of from 0.01 to 3 mmole/liter, together with a denaturing agent present in a concentration insufficient to denature said protein, for a period ranging from 1 hour to 300 hours.

4. Method of claim 3, wherein said GSH concentration is from 0.2 to 10 mmol/liter and said GSSG concentration is from 0.05 to 1 mmol/liter.

5. Method of claim 4, wherein said denaturing agent comprises at least one member selected from the group consisting of arginine, guanidine hydrochloride and a compound of the formula $$R_2-CO-NRR_1$$

wherein R and $R_1$ are hydrogen or $C_1$-$C_4$ alkyl, and $R_2$ is hydrogen, $NRR_1$ or $C_1$-$C_3$ alkyl.

6. Method of claim 3, wherein said denaturing agent comprises at least one member selected from the group consisting of arginine, guanidine hydrochloride and a compound of the formula $$R_2-CO-NRR_1$$

wherein R and $R_1$ are hydrogen or $C_1$-$C_4$ alkyl, and $R_2$ is hydrogen, $NRR_1$ or $C_1$-$C_3$ alkyl.

7. Method of claim 6, wherein said denaturing agent is selected from the group consisting of arginine and guanidine chloride.

8. Method of claim 7, wherein said denaturing agent is present in an amount ranging from 0.1 to 1.0 mole/liter.

9. Method of claim 7, wherein said denaturing agent is present in an amount ranging from 0.25 to 0.8 mole/liter.

10. Method of claim 6, wherein said denaturing agent is $R_2-CO-NRR_1$.

11. Method of claim 10, wherein said denaturing agent is present in an amount ranging from 0.5 to 4 mole/liter.

12. Method of claim 10, wherein said denaturing agent is present in an amount ranging from 1.0 to 3.5 mole/liter.

13. Method of claim 1, wherein said buffer further comprises a non-proteolytic protein.

14. Method of claim 13, wherein said non-proteolytic protein is bovine serum albumin.

15. Method of claim 1 or 5, further comprising reactivating said protein in the presence of EDTA in an amount ranging from 1 to 10 mmole/liter.

16. Method of claim 1, comprising digesting said cell sample by ultrasonics, high pressure dispersion or lysozyme.

17. Method of claim 16, further comprising digesting said cell sample in an aqueous buffer solution having a pH ranging from neutral to weakly acidic.

18. Method of claim 17, wherein said aqueous buffer solution contains 0.1 mole/liter Tris.

19. Method of claim 1, further comprising separating insoluble components from said digestion product prior to solubilizing.

20. Method of claim 1, comprising solubilizing said digestion product at an alkaline pH in the presence of a mercaptan reducing agent and a denaturing agent.

21. Method of claim 20, further comprising solubilizing said digestion product in the presence of guanidine hydrochloride or a compound of formula $$R_2-CO-NRR_1$$

wherein R and $R_1$ are hydrogen or $C_1$-$C_4$ alkyl, and $R_2$ is hydrogen, $NRR_1$ or $C_1$-$C_3$ alkyl.

22. Method of claim 21, wherein said guanidine hydrochloride is present at a concentration of 6 mole/liter.

23. Method of claim 21, wherein said compound of formula $R_2-CO-NRR_1$ is present at a concentration of 8 mole/liter.

24. Method of claim 20, further comprising solubilizing said digestion product in the presence of DTE, mercaptoethanol, cysteine or GSH.

25. Method of claim 1, wherein said protein is an antibody or antibody fragment.

26. Method of claim 1, wherein said protein is tissue plasminogen activator or a deglycosylated form thereof that has tissue plasminogen activator activity.

27. Method for activating a protein produced in insoluble, inactive form by expression of a gene in a prokaryote, comprising:
(i) digesting a cell sample of said prokaryote which contains the protein in insoluble form,
(ii) recovering the insoluble, inactive protein,
(iii) solubilizing the insoluble, inactive protein under conditions favoring denaturing and reduction of said insoluble, inactive protein to form a solubilized protein,
(iv) dialyzing the solubilized protein against a buffer at a pH of from 1 to 4 which contains from 4 to 8 moles/liter guanidine chloride or from 6 to 10 moles/liter urea,
(v) adding GSSG to the solubilized, dialyzed protein under denaturing conditions to form a mixed disulphide product,
(vi) dialyzing the mixed disulphide product against a buffer containing guanidine hydrochloride or urea, and
(vii) treating a solution containing said mixed disulphide at a concentration of from 1 to 1000 ug/ml with (a) GSH at a concentration of from 0.1 to 5 mmol/liter, and (b) a denaturing agent present in a concentration insufficient to denature said mixed disulphide at a pH of from 6 to 10, for a period of from 1 to 300 hours so as to form an activated protein.

28. Method of claim 27, wherein said denaturing agent comprises at least one member selected from the group consisting of arginine, guanidine hydrochloride and a compound of the formula $$R_2-CO-NRR_1$$

wherein R and $R_1$ are hydrogen or $C_1$-$C_4$ alkyl, and $R_2$ is hydrogen, $NRR_1$ or $C_1$-$C_3$ alkyl.

* * * * *